US 9,933,352 B2

(12) United States Patent
Brueck et al.

(10) Patent No.: US 9,933,352 B2
(45) Date of Patent: Apr. 3, 2018

(54) SENSOR FOR DETECTING PARTICLES

(71) Applicant: Robert Bosch GmbH, Stuttgart (DE)

(72) Inventors: Marc Brueck, Bondorf (DE); Christian Doering, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 89 days.

(21) Appl. No.: 14/429,142

(22) PCT Filed: Aug. 28, 2013

(86) PCT No.: PCT/EP2013/067769
§ 371 (c)(1),
(2) Date: Mar. 18, 2015

(87) PCT Pub. No.: WO2014/048660
PCT Pub. Date: Apr. 3, 2014

(65) Prior Publication Data
US 2015/0253233 A1 Sep. 10, 2015

(30) Foreign Application Priority Data

Sep. 26, 2012 (DE) .................. 10 2012 217 428

(51) Int. Cl.
G01N 15/06 (2006.01)
F01N 11/00 (2006.01)
(Continued)

(52) U.S. Cl.
CPC ......... G01N 15/0656 (2013.01); F01N 11/00 (2013.01); G01M 15/102 (2013.01); G01N 27/04 (2013.01); F01N 2550/04 (2013.01)

(58) Field of Classification Search
CPC .... G01N 15/0656; G01N 27/04; F01N 11/00; F01N 2550/04; G01M 15/102
(Continued)

(56) References Cited

U.S. PATENT DOCUMENTS 4,313,338 A * 2/1982 Abe .................. G01N 27/12
338/34
5,440,189 A * 8/1995 Nakahata ............ G06G 7/195
310/313 A
(Continued)

FOREIGN PATENT DOCUMENTS

CN 102606266 A 7/2012
DE 10 2006 002 111 8/2006
(Continued)

OTHER PUBLICATIONS (English Translation) Heiner, Sensor element for a particle sensor, Jan. 2008, Bosch GMBH Robert.*
(Continued)

Primary Examiner — John Fitzgerald
Assistant Examiner — Truong D Phan
(74) Attorney, Agent, or Firm — Norton Rose Fulbright US LLP

(57) ABSTRACT

A sensor for detecting particles, in particular soot particles, includes at least two measuring electrodes and a heating element. The measuring electrodes are placed on a chip of an electrically insulating material, or on an electrically insulating intermediate layer that is on the chip. The sensor also includes a ceramic substrate upon which the heating element is configured. The chip is connected to the ceramic substrate and is made of a highly thermally conductive material.

20 Claims, 2 Drawing Sheets

(51) Int. Cl.
*G01M 15/10* (2006.01)
*G01N 27/04* (2006.01)

(58) Field of Classification Search
USPC .............. 73/23.33; 204/421; 356/237.3; 250/222.2, 370.02
See application file for complete search history.

(56) References Cited

U.S. PATENT DOCUMENTS

| | | | | |
|---|---|---|---|---|
| 7,208,077 | B1* | 4/2007 | Albers | G01N 27/3277 204/403.01 |
| 8,033,159 | B2* | 10/2011 | Fleischer | G01N 15/0656 73/28.01 |
| 2004/0233256 | A1* | 11/2004 | Hoisington | B41J 2/14201 347/68 |
| 2007/0158191 | A1* | 7/2007 | Berger | G01N 15/0656 204/421 |
| 2008/0092745 | A1* | 4/2008 | Tsao | B01D 46/0038 96/224 |
| 2009/0013758 | A1* | 1/2009 | Baumann | F01N 11/00 73/23.33 |
| 2009/0090622 | A1* | 4/2009 | Ripley | G01N 15/0656 204/401 |
| 2009/0217737 | A1* | 9/2009 | Dorfmueller | F01N 11/00 73/28.01 |
| 2011/0102724 | A1* | 5/2011 | Ono | G02F 1/133514 349/143 |
| 2011/0156727 | A1* | 6/2011 | Achhammer | F02D 41/1466 324/691 |
| 2011/0260219 | A1* | 10/2011 | Wahl | G01N 27/4141 257/253 |

FOREIGN PATENT DOCUMENTS

| | | |
|---|---|---|
| DE | 102006032741 A1 | 1/2008 |
| DE | 10 2006 048 354 | 4/2008 |
| DE | 102008007664 A1 | 8/2009 |
| DE | 102010038758 A1 | 2/2012 |
| DE | 102010044308 A1 | 3/2012 |
| WO | WO 2004/097392 | 11/2004 |

OTHER PUBLICATIONS

International Search Report for PCT/EP2013/067769, dated Dec. 16, 2013.

* cited by examiner

SENSOR FOR DETECTING PARTICLES

BACKGROUND

Numerous methods and devices for detecting particles, such as soot or dust particles, are known from the related art.

It is known in the art to use two electrodes placed on a ceramic material to measure a concentration of particles, such as soot or dust particles, in an exhaust gas. This may be accomplished, for example, by measuring the electrical resistance of the ceramic material that separates the two electrodes. To be more precise, the electric current, which flows between the electrodes in response to the application of an electric voltage thereto, is measured. Electrostatic forces cause the soot particles to be deposited between the electrodes and, over time, to form electrically conductive bridges therebetween. The more of these bridges that are present, the more the measured current increases. The result is an increased short-circuiting of the electrodes.

Sensors of this kind are used, for example, in an exhaust branch of an internal combustion engine, such as in a diesel combustion engine. These sensors are usually located downstream of the exhaust valve, for example, downstream of the diesel particulate filter. In the future, heightened environmental awareness, as well as legal regulations will necessitate that the soot emissions be monitored during operation of a motor vehicle and that the functionality of the exhaust-gas aftertreatment devices, such as a particulate filter, be assured, for example. This type of monitoring of the functionality is generally referred to as on-board diagnostics. The loading level of diesel particulate filters must also be predictable. A resistive soot sensor provides one practical way of doing this. It uses the change in the resistance of an interdigital electrode structure caused by soot deposits to detect the soot. Due to the operating principle thereof, the resistive soot sensor is classified under the accumulative sensing principles.

The German Patent Application DE 10 2006 002 111 A1 describes a soot particle sensor, for example, that is constructed using a ceramic multilayer technology, i.e., from a plurality of superposed layers. The multilayer technology makes possible a compact and rugged design where the functions of soot sensing, heating and temperature sensing can be realized on different superposed planes. The interdigital electrodes of platinum are placed on the top side of the ceramic substrate using screen printing techniques. Between these, soot bridges form by the application of an electric potential difference, the sensor signal, therefore, being generated in response to a short circuit. The sensitivity of the sensor is essentially limited by the distance between the interdigital electrodes, the smallest possible distance being desired.

In spite of the numerous advantages of the known, related art methods and devices for detecting particles, they still have potential for improvement. The above described ceramic sensor design has a comparatively low thermal conductivity, for example. Accordingly, the heating element must be adapted for a higher heating power to ensure a temperature that suffices for burning off accumulated particulate from the sensor and for providing the required dynamic response. Current consumption is thereby increased. In addition, the electrical signal current on the order of μA, which can be obtained using these sensors, requires a potential difference of more than 40 V, so that the signal processing necessitates a separate control unit. Therefore, the application of the sensor proves to be complex. Manufacturing sensors of materials, such as silicon, does, in fact, allow a fine structuring in a photolithographic process of the interdigital electrode measuring region and, thus, makes it possible to do without a sensor control unit to achieve cost advantages. In terms of process technology, however, the substantially greater thermal conductivity in comparison to ceramic entails considerable outlay to thermally insulate the interdigital electrode measuring region well enough to maintain the manageability of the heating power required for the regeneration process. Moreover, silicon is too expensive to use as a material in sensor regions where the advantages thereof do not have any effect, or where other properties, such as brittleness, are rather even disadvantageous.

SUMMARY

Without limiting other specific embodiments and applications, the present invention is described in the following, in particular with reference to sensors for detecting particles, in particular soot particles in an exhaust-gas stream of an internal combustion engine.

Example embodiments of the present invention provide a sensor for detecting particles, e.g., soot particles, that is able to at least substantially overcome the disadvantages of known sensors.

According to an example embodiment of the present invention, a sensor for detecting particles, in particular soot particles, includes at least two measuring electrodes and one heating element, the measuring electrodes being placed on a chip of an electrically insulating material, the sensor also including a ceramic substrate upon which the heating element is provided, the chip being connected to the ceramic substrate.

The ceramic substrate can feature a recess in which the chip is positioned, and can be designed for the chip to be fixed in position in the recess. The measuring electrodes can be electrically contactable via the ceramic substrate, in particular via at least two conductor tracks on the ceramic substrate. The measuring electrodes can be configured to intermesh. They can also be configured in a circular and/or star shape on the chip. The ceramic substrate can partially cover a surface of the chip upon which the measuring electrodes are configured, for example, in a way that exposes a circular, oval, rectangular or polygonal region of the chip surface, in which region the electrodes are positioned. The ceramic substrate can include a layered structure, which can include at least one first layer upon which the heating element is positioned, and at least one second layer configured to partially cover a surface of the chip upon which the measuring electrodes are positioned. The second layer can feature conductor tracks for electrically contacting the measuring electrodes. The ceramic substrate can be rounded toward a surface of the chip on which the measuring electrodes are disposed. The chip can contact the heating element. The chip can have a thickness of 500 μm to 800 μm, preferably 550 μm to 750 μm, and even more preferably 600 μm to 700 μm. The chip can have a width of 2 mm to 4 mm, preferably 2.5 mm to 3.5 mm, and even more preferably 2.75 mm to 3.25 mm. The chip can be at least partially fabricated of an inorganic semiconductor material. It can be essentially fabricated of silicon, for example.

The particles discussed herein can be, for example, electrically conductive particles, such as soot or dust particles, in particular.

In example embodiments of the present invention, the measuring electrodes are suited for a current-voltage measurement, which, in the context of the present invention, means a measurement where either a specific electric voltage is applied to the measuring electrodes, and an electric current flow between the measuring electrodes is measured, or where an electric current is applied to the measuring electrodes, and an electric voltage between the measuring electrodes is measured. A current-voltage measurement can be a resistance measurement, for example, a resistance of the structure composed of the measuring electrodes and the substrate being measured. In an example embodiment, a voltage controlled and/or regulated measurement, and/or a current controlled and/or regulated measurement is carried out, where the current and/or voltage is applied in the form of a continuous signal and/or in the form of a pulsed signal. Thus, a direct-current voltage and/or a direct current can be applied, and a current response and/or a voltage response, respectively, is recorded. Alternatively, a pulsed voltage and/or a pulsed current is applied, and a current response and/or a voltage response, respectively, is recorded.

Therefore, in the context of the present invention, a measured quantity is a quantity ascertained by the current-voltage measurement and which, accordingly, can be an electric current or an electric voltage. An electrical resistance derived therefrom can also be used as a measured quantity.

In the context of the present invention, interdigital electrodes are electrodes that are configured to intermesh, in particular in a comb-like manner.

In the context of the present invention, an electrically insulating material is understood to be a material suited for preventing a current flow, for example, a ceramic material, such as, for example, silicon, aluminum oxide, and/or zirconium oxide.

A heating element in the context of the present invention is an element that is suited for heating the sensor in a way that removes the particles that have collected between the measuring electrodes. This can be accomplished by electrical energy, for example, that is converted into Joulean heat. For example, the heating element is in the form of a resistive heating element, e.g., an electrical resistor track. An electric voltage, which leads to a current flow through the conductor tracks of the heating element, is applied to the heating element, for example. The electrical resistance of the conductor tracks induces heat generation. The heat is released, inter alia, to regions of the substrate between the measuring electrodes in which the particles have deposited. Temperatures of approximately 700° C. are reached.

A chip in the context of the present invention is an unhoused substrate in a cuboid or plate form. Such a "bare chip" can be obtained by sawing or breaking a finish-machined wafer into rectangular sections upon which a complete, functioning component, such as the measuring electrodes, is situated, for example.

In the context of the present invention, a ceramic substrate also encompasses a multilayer structure. This means that the ceramic substrate can be composed of a plurality of layers, respectively films. A layer is a two-dimensional extent of a uniform material at a certain height that can be disposed above, between, underneath or on other components.

A thickness of the chip, as referred to herein, is a dimension that is parallel to an arrangement direction in which the layers are stacked and orthogonal to the largest surfaces of each of the superposed layers.

A width of the chip, as referred to herein, is a dimension disposed orthogonally to the thickness dimension and orthogonally to an extension of the length of the sensor layers.

Manufacturing from "essentially" one material, as referred to herein, is a manufacturing of the particular component from at least 70% by volume of this material. For example, the statement that "the component is essentially made of silicon" connotes that the component is manufactured at least 70% by volume of silicon.

In the context of the present invention, the ceramic multilayer structure, which provides a certain thermal and mechanical ruggedness and low thermal conductivity, combines the advantages thereof with those of silicon technology, in particular micro-patternability. A silicon component that is optimal for the measuring function is integrated in a ceramic substrate. In particular, the micro-patterning for improving responsivity is limited to a silicon chip that merely contains the measuring electrodes and, as such, is inserted immovably into a corresponding recess in the ceramic structure. Here, the advantage is derived that silicon, as an expensive material, is only used where it provides functional advantages, thereby increasing the yield of silicon chips per wafer. Using known methods, platinum is applied in a thin layer by sputter deposition to the silicon chip and photolithographically patterned, making it possible to realize structure sizes, such as gaps and electrode widths, of up to 1 μm. This measure makes it possible to achieve a sensor signal current on the order of 1 mA at a potential difference of 12 V, and, depending on the design of the measuring electrode structure, it is also possible to realize significantly lower triggering times than in the case of a ceramic element, such as 30 s, for example, in comparison to 300 s for conventional sensors. Moreover, depending on the temperature level, silicon, as a chip material, has 15 to 30 times greater thermal conductivity and, altogether, a higher thermal conductance than ceramic material, such as zirconium dioxide, for example, thereby resulting in a more homogeneous temperature distribution, accompanied at the same time by a faster heating-up time during the heating process for the regeneration cycle in the region of the measuring electrodes. To limit the maximum heat power required for the regeneration process, it is important that the remaining regions of the bar-shaped sensor have a low thermal conductivity to minimize the flow of heat power into the housing. This is ensured by the use of ceramic as a substrate material for the silicon chip.

Other example details and features of example embodiments of the present invention are described and can be derived from the following description of preferred example embodiments schematically illustrated in the figures.

DETAILED DESCRIPTION

Figure 1:
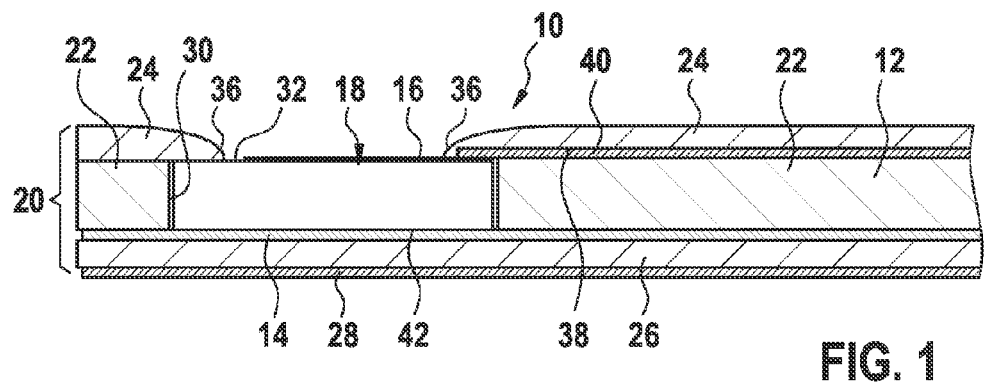
FIG. 1 shows a cross-sectional view along a longitudinal direction of a sensor for detecting particles, according to an example embodiment of the present invention.

FIG. 1 shows a cross-sectional view of a sensor 10 for detecting particles, in particular soot particles in a gas stream, such as an exhaust-gas stream of an internal combustion, for example, that is used for installation in an exhaust branch of a motor vehicle. Sensor 10 is designed as a soot sensor, for example, and is preferably configured downstream of a soot filter of a motor vehicle that includes a diesel combustion engine.

Sensor 10 includes a substrate 12 that is constructed using a ceramic material, such as zirconium dioxide, for example, and is therefore a ceramic substrate. In addition, sensor 10 includes a heating element 14 and two measuring electrodes 16. Measuring electrodes 16 are placed on a chip 18 of an electrically insulating material. Measuring electrodes 16 can also be located on an insulating, thin intermediate layer that is deposited on the surface of chip 18. Chip 18 can, in particular, be at least partly made of an inorganic semiconductor material. Chip 18 is essentially fabricated of silicon, for example. In the illustrated specific embodiment, chip 18 is completely made of silicon, for example.

In particular, ceramic substrate 12 includes a layered structure 20 composed of a first layer 22, a second layer 24, and a third layer 26. In the longitudinal sectional representation of FIG. 1, first layer 22 and third layer 26 surround heating element 14 in a sandwich-like configuration. It is understood, however, that heating element 14 is actually integrated between first layer 22 and third layer 26 in a way that allows heating element 14 to be surrounded on all sides by first layer 22 and third layer 26. In the illustrated example embodiment, a temperature sensor 28 is configured on the side of third layer 26 facing away from heating element 14.

Figure 3:
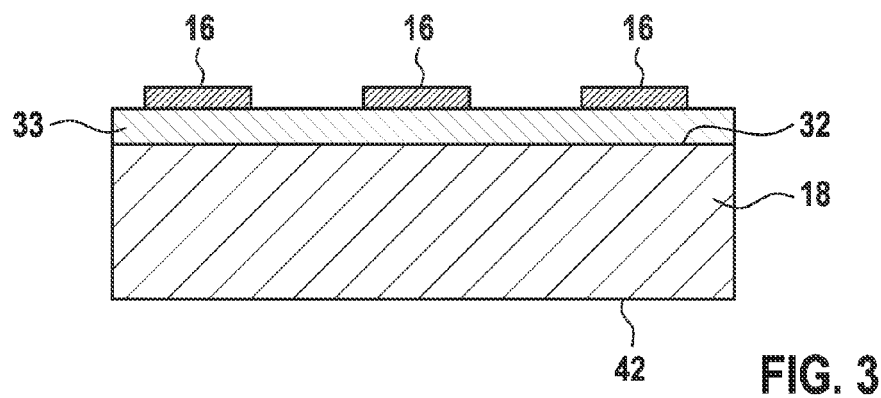
FIG. 3 shows a cross-sectional view of the chip, according to an example embodiment of the present invention.
Figure 4:
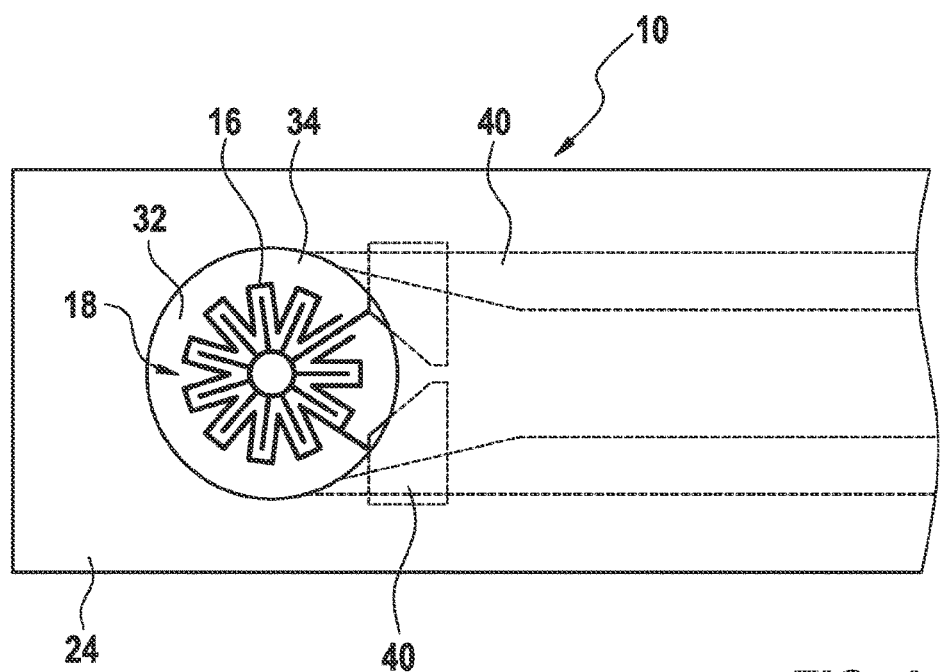
FIG. 4 shows a plan view of the sensor for detecting particles, according to an example embodiment of the present invention.

Chip 18 is located in a recess 30 in first layer 22. Heating element 14 and chip 18 do not necessarily need to be configured in the same ceramic layer 22 of layered structure 20. As may be inferred from the illustrations of FIGS. 2 and 3, chip 18 is essentially cuboidal. A thickness of chip 18 is 500 μm to 800 μm, for example, preferably 550 μm to 750 μm, and even more preferably 600 μm to 700 μm, for example 675 μm. The thickness of chip 18 is a dimension parallel to a stacking direction of layers 22, 24, 26 and extends in the representation of FIG. 1 from top to bottom. A width of chip 18 is 2 mm to 4 mm, preferably 2.5 mm to 3.5 mm, and even more preferably 2.75 mm to 3.25 mm, for example 3.0 mm. The width of chip 18 is a dimension in parallel to an extension of the lengths of layers 22, 24, 26, and orthogonal to both the stacking direction of layers 22, 24, 26 and the drawing plane of FIG. 1 (the width extends from top to bottom in the representation in FIG. 4).

A thin oxide layer 33, a thickness of which is, for example, 2.5 μm can be disposed on a surface 32 of chip 18 on which measuring electrodes 16 are positioned. Oxide layer 33 reliably electrically insulates measuring electrodes 16 and, in the case of silicon, serves as a substrate material for chip 18 of silicon dioxide which, as what is commonly known as thermal oxide, grows at a high temperature of approximately 1000° C. in a time-controlled manner to a thickness of up to 5 μm. Measuring electrodes 16 can be configured in a circular and/or star shape, for example, on chip 18. A thickness of measuring electrodes 16 can be, for example, 150 nm. Measuring electrodes 16 are applied in a thin layer process by sputter deposition and photolithographically patterned on surface 32, for example. Measuring electrodes 16 are present in the form of a platinum thin layer, for example.

Figure 2:
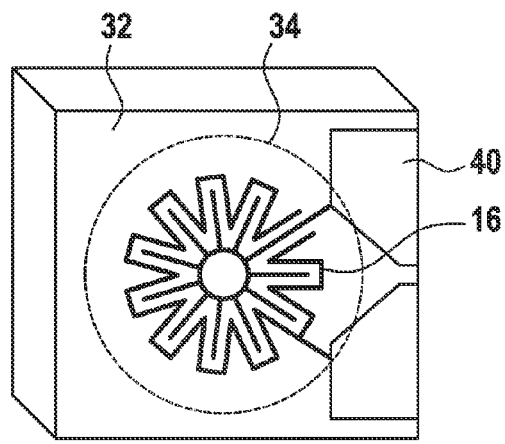
FIG. 2 shows a perspective view of a chip, according to an example embodiment of the present invention.

Measuring electrodes 16 can be configured with a bar-shaped configuration. Alternatively, as shown in FIG. 2, measuring electrodes are configured in a star-shaped configuration, which is preferred for stagnation point flows incident to surface 32 and sensor 10 since they have a potential for faster response times and greater responsivity. It is understood, however, that a linear configuration, respectively a comb-like intermeshing of measuring electrodes 16 is possible. A structure of this kind is suited, for example, for a longitudinal flow incident to sensor 10.

Referring back to FIG. 1, it is shown that second layer 24 partially covers surface 32 of chip 18. For example, second layer 24 can partially cover surface 32 in a way that exposes a circular region 34 of surface 32, as shown exemplarily in FIGS. 2 and 4. Region 34 can alternatively be of an oval, rectangular or polygonal form. Measuring electrodes 16 are configured within exposed region 34. In addition, second layer 24 can be rounded to slope toward surface 32, for example, shaped as a rounded step portion 36. In addition, on bottom side 38 of second layer 24, i.e., that side which faces first layer 22, two conductor tracks 40 are provided for electrically contacting measuring electrodes 16. As indicated in FIGS. 1 and 2, conductor tracks 40 partially cover surface 32 of chip 18 in a way that allows them to be electrically contacted by measuring electrodes 16.

Ceramic substrate 12 and, in particular, second layer 24 fix chip 18 in position in recess 30. By a surface 42, which is a bottom side of chip 18 facing opposite measuring electrodes 16 and surface 32, chip 18 makes contact with heating element 14, so that heating power introduced by heating element 14 can arrive directly in chip 18 and reach measuring electrodes 16.

In an example embodiment, entire sensor 10 is 1 mm thick, 4 mm wide and 60 mm long, for example, where a length or direction of longitudinal extent of the sensor is a dimension from left to right and vice versa in the representation of FIG. 1. Together, measuring electrodes 16, heating element 14, and temperature sensor 28 have a thickness of 10 μm to 20 μm, for example 15 μm. Chip 18 can be manufactured separately from the remaining components of sensor 10, such as layers 22, 24, 26, heating element 14, temperature sensor 28, etc. Measuring electrodes 16 may be manufactured separately on chip 18, for example, i.e., before chip 18 is inserted into recess 30. However, it is likewise possible for measuring electrodes 16 to be manufactured following insertion of chip 18. Measuring electrodes 16 are applied in the form of the thin platinum layer mentioned above with a layer thickness of 150 nm, for example. Chip 18 prepared in this manner can then be inserted into recess 30 of substrate 12. Second layer 24 is used as a protective film, for example, in order to fix chip 18 in position. On the other hand, conductor tracks 40 for electrically contacting measuring electrodes 16 are applied to the bottom side of second layer 24. Conductor tracks 40, as well as the contact surfaces of measuring electrodes 16 on surface 32 of chip 18 are dimensioned in a way that enables mutual coverage to be ensured under all conditions, taking into account all tolerances, such as the clearance fit of recess 30 for chip 18.

First layer 22, in turn, features recess 30 that is advantageously adapted to the contour of chip 18 and ensures a sufficient overlap region with silicon chip 18. This enables it to be reliably fixed in position following assembly and subsequent sintering. In particular, in the case of an adapted thickness of first layer 22, it is achieved that the contraction of ceramic substrate 12 during sintering leads to a desired prestressing and thus to an efficient contacting of chip 18 and of measuring electrodes 16. As mentioned above, chip 18 rests, by bottom side thereof, directly on heating element 14, so that no appreciable losses arise during transition of the heating power. The design of rounded step portion 36 may be preferred since, in this case, a flow runs from radially inwardly to outwardly, uninterrupted, along measuring electrodes 16, while, in the case of a longitudinal incident flow, the upstream step portion represents a disturbance which, under certain circumstances, influences the sensor signal.

In addition, sensor 10 can include a housing that surrounds the structure shown in FIG. 1, but which is not shown in FIG. 1 in order to simplify the explanation of the design of sensor 10. The housing can be in the form of a catch sleeve, for example, that is provided with an opening in the region disposed above measuring electrodes 16 and is used for stabilizing a gas stream flowing in the exhaust branch, so that soot particles, or other particles contained in the gas stream, preferably form deposits in the region of measuring electrodes 16.

In an example embodiment, sensor 10 shown in FIG. 1 is configured to function in the following manner: in response to soot particles, or other electrically conductive particles, forming deposits on surface 32 of chip 18, an electrical resistance between the two measuring electrodes 16 is reduced. The particles, in particular soot particles, that form a deposit under the action of an electrical measuring voltage, short circuit the measuring electrodes that intermesh in a comb-like manner, and a decreasing resistance and increasing current between measuring electrodes 16 is measurable when the voltage is constantly applied. This can be ascertained by a current-voltage measurement. For example, by measuring an impedance between the two measuring electrodes 16, characteristics are obtained that are typical for what is generally referred to as an RC element. This signifies that the concentration of soot or other particulates in the exhaust gas in question can be determined on the basis of the change in the resistance component of the RC element as a function of time.

To regenerate sensor 10, heating element 14, which is integrated in ceramic substrate 12, can burn off the accumulated particulates following a certain time period. Assuming that sensor 10 is functional, the resistance between measuring electrodes 16 should significantly increase and preferably tend towards infinity following this process, commonly referred to as "baking out."

What is claimed is:

1. A sensor for detecting particles, the sensor comprising:
    a chip including an electrically insulating material, wherein the chip is at least partially fabricated of an inorganic semiconductor material capable of conducting electricity;
    at least two measuring electrodes on the chip;
    a ceramic structure that includes:
        a first layer made of a ceramic material,
        a second layer made of the ceramic material, and
        a third layer made of the ceramic material, the first layer being disposed between the second layer and the third layer such that a top surface of the first layer faces a bottom surface of the second layer and a bottom surface of the first layer faces a top surface of the third layer; and
    a heating element disposed between the first layer and the third layer, wherein:
        the first layer includes a recess having a height and a width sized to receive the chip,
        the recess is defined by a bottom side, lateral sides, and an opening opposite the bottom side,
        the second layer includes an opening that is aligned with the opening of the recess, and
        the chip is inserted in the recess so that at least a portion of a top surface of the chip is exposed to and in direct contact with an external environment through the opening of the recess and through the opening of the second layer.

2. The sensor of claim 1, wherein the chip is fixed in the recess.

3. The sensor of claim 1, wherein a shape of the ceramic structure is such that the ceramic structure fixedly traps the chip within the ceramic structure.

4. The sensor of claim 1, wherein the measuring electrodes are electrically contactable from outside of the ceramic structure.

5. The sensor of claim 1, wherein the measuring electrodes are exposed through the opening of the recess and the opening of the second layer of the ceramic structure, and wherein the measuring electrodes are disposed on a region of the chip aligned with the opening of the recess and the opening of the second layer of the ceramic structure such that a vertical axis that intersects the region of the chip does not intersect the second layer of the ceramic structure and does not intersect the first layer of the ceramic structure.

6. The sensor of claim 1, wherein the opening of the second layer of the ceramic structure is circular or oval.

7. The sensor of claim 1, wherein the opening of the second layer of the ceramic structure is polygonal-shaped.

8. The sensor of claim 1, wherein the second layer of the ceramic structure is rounded to slope as a rounded step portion toward a surface of the chip on which the measuring electrodes are disposed.

9. The sensor of claim 1, wherein the chip is in contact with the heating element.

10. The sensor of claim 1, wherein the sensor is configured to detect soot particles.

11. The sensor of claim 1, wherein a top surface of the second layer of the ceramic structure is above the top surface of the chip along a vertical direction.

12. The sensor of claim 1, further comprising a temperature sensor disposed on a bottom surface of the third layer of the ceramic structure.

13. The sensor of claim 1, wherein a bottom surface of the chip directly contacts the heating element.

14. The sensor of claim 1, wherein the measuring electrodes are in direct contact with the top surface of the chip and are exposed to the external environment.

15. The sensor of claim 1, wherein the measuring electrodes are electrically contactable via at least two conductor tracks that are on the ceramic structure.

16. The sensor of claim 15, wherein the conductor tracks are disposed on the bottom surface of the second layer of the ceramic structure.

17. The sensor of claim 15, wherein conductor tracks by which the measuring electrodes are electrically contactable are included in the second layer of the ceramic structure.

18. The sensor of claim 1, wherein the measuring electrodes intermesh with each other.

19. The sensor of claim 18, wherein the measuring electrodes are configured in a circular shape on the chip.

20. The sensor of claim 18, wherein the measuring electrodes are configured in a star shape on the chip.

* * * * *